ically active polymeric materials such as photographic image dye-providing materials. As one example, such compounds.

United States Patent [19]

MacGregor et al.

[11] Patent Number: 4,656,286
[45] Date of Patent: Apr. 7, 1987

[54] AMINOETHANETHIOL AND THIAZOLIDINE COMPOUNDS

[75] Inventors: Paul T. MacGregor, Lexington; Myron S. Simon, West Newton, both of Mass.

[73] Assignee: Polaroid Corporation, Patent Dept., Cambridge, Mass.

[21] Appl. No.: 866,782

[22] Filed: May 23, 1986

Related U.S. Application Data

[63] Continuation of Ser. No. 644,913, Aug. 27, 1984, abandoned.

[51] Int. Cl.$^4$ ............... C07D 277/04; C07C 149/273; C07C 149/253
[52] U.S. Cl. .................................. 548/146; 260/508; 560/18; 562/432; 564/153; 564/154; 564/389; 564/390
[58] Field of Search ............ 548/146; 560/18; 562/432; 260/508; 564/153, 154, 389, 390

[56] References Cited

PUBLICATIONS

Dannals et al, Appl. Nucl. Radiochem., pp. 127–138, Pergamon CA98(7): 49644a.
Takatori et al, Yakugaku Zasshi, 88, No. 3, Mar. 1968, pp 360–365.

*Primary Examiner*—Robert Gerstl
*Attorney, Agent, or Firm*—Gaetano D. Maccarone

[57] ABSTRACT

There are disclosed certain aminoethanethiols, and salts thereof, and certain thiazolidines which are made therefrom. The compounds are useful as intermediates in the synthesis of photographic image dye-providing materials.

4 Claims, No Drawings

AMINOETHANETHIOL AND THIAZOLIDINE COMPOUNDS

This is a continuation of application Ser. No. 644,913, filed 8-27-84 abandoned.

BACKGROUND OF THE INVENTION

This application relates to aminoethanethiol compounds and to thiazolidine compounds which are made therefrom. These compounds are useful as intermediates in the preparation of image dye-providing materials for use in photographic applications.

U.S. Pat. No. 3,719,489 describes and claims photographic processes employing initially photographically inert compounds which are capable of undergoing cleavage in the presence of the imagewise distribution of silver ions made available during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer. Color-providing compounds useful in the above processes form the subject matter of U.S. Pat. No. 4,098,783, a continuation-in-part, of said U.S. Pat. No. 3,719,489.

Copending application Ser. No. 644,915, filed on even date herewith now U.S. Pat. No. 4,535,051, discloses photographic processes for forming a dye image from a color shifted dye precursor which comprises a dye having at least one acylated amino group and which also includes a moiety containing a thiazolidin-2-yl group which upon silver-assisted cleavage initiates a reaction sequence leading to the formation of the image dye. The present application is directed to aminoethanethiol and thiazolidine compounds which are useful as intermediates in the preparation of image dye-providing materials suitable for use in such photographic processes.

SUMMARY OF THE INVENTION

It is an object of the invention to provide compounds which are useful as intermediates in the preparation of image dye-providing materials.

It is another object of the invention to provide novel aminoethanethiol compounds.

It is still another object to provide salts of the aminoethanethiols.

A further object is to provide novel thiazolidine compounds.

BRIEF SUMMARY OF THE INVENTION

These and other objects and advantages are accomplished in accordance with the invention by providing aminoethanethiols which are represented by the formula

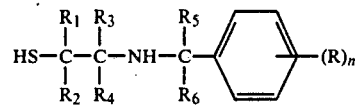

wherein R may be any group which confers wettability or solubility in aqueous alkali such as $-COOR_7$, $-CONHR_7$, $-OH$, $-SO_3H$ or $-SO_3R_8$; $R_1-R_6$ may each independently be hydrogen or alkyl, preferably having from 1 to 6 carbon atoms; $R_7$ is hydrogen or alkyl, preferably having from 1 to 6 carbon atoms, $R_8$ is an alkali metal; and n is an integer of from 1 to 3; and the salts thereof.

The salts may be acid salts in which case they may be represented by the formula

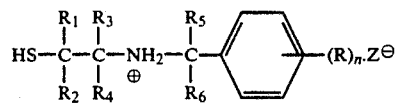

where Z is an anion such as chloride, bromide, iodide, sulfonate, tetraphenylborate, etc. The salts may also be internal salts in which case the anion is incorporated in the molecule such as is illustrated by the formula

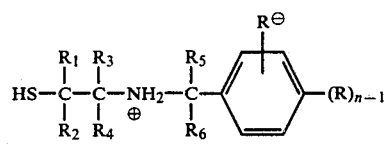

where $R\ominus$ is an anion derived from R such as $-COO\ominus$, $-SO_3\ominus$ or $-O\ominus$. In a prefered embodiment where R is $-OH$ and n is 2 or 3, the hydroxy substituents are positioned meta to each other so as not to form a silver halide developing moiety.

The thiazolidine compounds which can be formed from the aminoethanethiols are represented by the formula

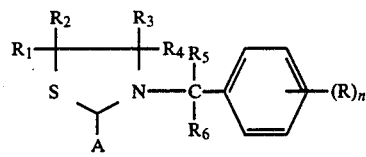

where A is hydrogen, alkyl, preferably having from 1 to 6 carbon atoms, aryl such as phenyl or naphthyl, aralkyl such as benzyl or phenethyl, alkaryl or mono- and di-substituted derivatives thereof which are substituted with substituents such as alkyl, alkoxy, hydroxy, dimethylamino or halogen; and $R-R_6$ and n are as previously defined.

It has been found that when $R_3$ and $R_4$ are each methyl the photographic image dye-providing materials which are prepared from the thiazolidine compounds typically exhibit better alkali stability. Further, it has been found that when R is —COOR₇ and n is 2 and the —COOR₇ groups are attached to the 3- and 5- positions of the benzene ring, the image dye-providing materials which are made therefrom have better alkali solubility which is desirable. Accordingly, such compounds constitute preferred embodiments.

DESCRIPTION OF THE PREFERRED EMBODIMENTS

The compounds of the invention can be prepared by reactions which are known in the art and these will be apparent particularly in view of the specific examples provided below herein.

The invention will now be described further in detail by way of examples it being understood that these are intended to be illustrative only and the invention is not intended to be limited to the materials, conditions, process parameters, etc., which are recited therein.

EXAMPLE I

An ester (15 g) of the formula

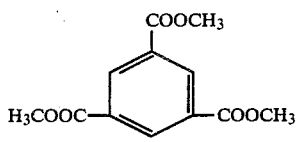

was stirred in 200 ml of tetrahydrofuran and cooled to 0° C. A solution of lithium hydridotri(t-butoxy) aluminate (31 g) in 200 ml of tetrahydrofuran was added dropwise to the ester solution and stirring continued for about 48 hours at room temperature. The reaction mixture was then heated to reflux (65° C.) for three hours, cooled to 2° C. and filtered to remove a white solid. The filtrate was added to about 900 ml of ice water containing about 25 ml of conc. HCl and extracted with methylene chloride. The methylene chloride extract was washed with water, dried over MgSO₄, filtered and evaporated to give a white solid which was recrystallized from about 40 ml of toluene to give 6 g of the desired alcohol ester, a white solid. The toluene filtrate was cooled in an ice bath to yield an additional 2.5 g of the desired product, a white solid of the formula

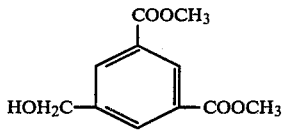

The structure was confirmed by spectral analysis.

Triflic anhydride (1.50 ml) was stirred with 20 ml of methylene chloride under nitrogen at 0° C. The alcohol ester (2 g), diisopropylethylamine (1.56 ml), and 20 ml of methylene chloride were combined in an addition funnel and added in very small portions to the anhydride solution over a 2 hour period with the temperature being held under 5° C. 2,4,4-trimethylthiazoline (1.15 ml) was added all at once and the reaction mixture left to stir overnight. The solution was evaporated and the residue washed twice with hot cyclohexane. The residue was crystallized from tetrahydrofuran to give 1 g the desired product having the formula

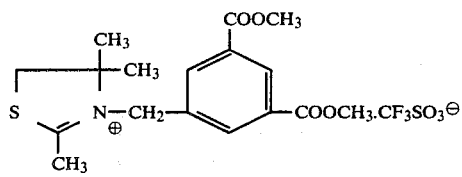

The crude thiazolinium salt was recrystallized from about 10 ml of tetrahydrofuran.

$C_{18}H_{22}F_3N\ O_7S_2$ requires 44.53% C, 4.57% H, 11.74% F, 2.89% N and 13.21% S. Elemental analysis found 44.28% C, 4.67% H, 11.61% F, 2.87% N and 13.26% S.

The thiazolinium salt (45 g) was mixed with 200 ml of distilled water and 25 ml of conc. HCl and heated to reflux for about 25 hours. The reaction mixture was filtered and the filtrate cooled and then filtered to recover a white solid which was dried under vacuum at room temperature to give the desired product, an aminoethanethiol of the formula

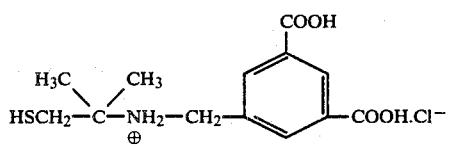

Spectral analysis and elemental analysis confirmed the structure.

$C_{13}H_{18}N\ O_4\ S\ Cl.\ H_2O$ requires 46.21% C, 5.97% H, 4.15% N, 9.49% S and 10.50% Cl. Elemental analysis found 46.56% C, 5.79% H, 4.14% N, 9.74% S and 10.81% Cl.

EXAMPLE II

The aminoethanethiol salt of Example I (5 g) was combined with 50 ml of methanol, which had been previously saturated with HCl gas, and heated to reflux overnight. The reaction mixture was filtered to recover the precipitate which was washed with methanol and dried under vacuum to give 4.2 g of the methyl diester of the aminoethanethiol hydrochloride salt.

The aminoethanethioldiester hydrochloride (1.0 g), p-aminobenzaldehyde (0.43 g), anhydrous potassium carbonate (0.4 g) and 5 ml of ethanol were combined under nitrogen and refluxed for about 72 hours. The reaction mixture was filtered and the filtrate cooled and evaporated. The residue was triturated with methanol to give 0.522 g of crude product which was recrystallized from methanol to give 0.39 g of the desired thiazolidine, a pale yellow solid, m.p. 111°–113.5° C. having the formula

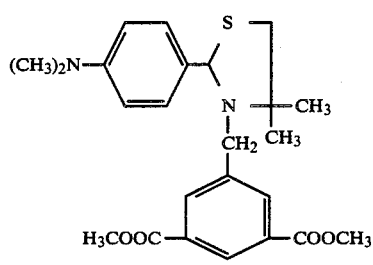

The structure was confirmed by spectral analysis.

The thiazolidine diester (0.368 g) was dissolved in 3.3 ml of dioxane and 2N NaOH (0.83 ml, 1.6 mm) was added, dropwise with stirring, to form a two phase mixture which was stirred overnight. The solution was treated with 0.1 ml of acetic acid in 1 ml of water and several drops of conc. HCl. Potassium bicarbonate solution was added to bring the pH to about 6. The light yellow precipitate was recovered by filtration, washed with water, and dried at 50° C. under vacuum for five hours to give 0.283 g of crude product. This product was crystallized from ethanol to give 0.189 g of the thiazolidine dicarboxylic acid represented by the formula

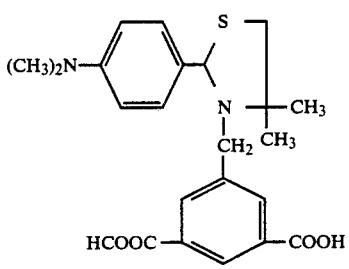

The structure was confirmed by spectral analysis.

EXAMPLE III p-Dimethylaminobenzaldehyde (149 mg), and aminoethanethiol (320 mg) of the formula

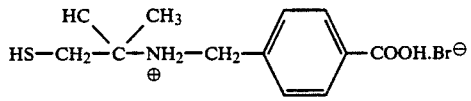

and sodium bicarbonate (84 mg) were combined with 5 ml of absolute ethanol with stirring under nitrogen and heated to reflux for one hour. The reaction mixture was filtered and the filtrate cooled. The resulting precipitate was collected by filtration and washed with ethanol to give a white solid. The solid was recrystallized from ethanol and dried overnight to give the desired thiazolidine a white solid of the formula

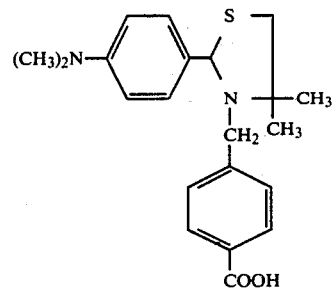

The structure was confirmed by spectral and elemental analysis.

$C_{21} H_{25} N_2 O_2 S$ requires 68.08% C, 7.07% H, 7.56% N, and 8.64% S. Elemental analysis found 67.99% C, 7.14% H, 7.63% N and 8.81% S.

Although the invention has been described with respect to specific preferred embodiments, it is not intended to be limited thereto but rather those skilled in the art will recognize that variations and modifications may be made therein which are within the spirit of the invention and the scope of the appended claims.

What is claimed is:

1. A compound represented by the formula

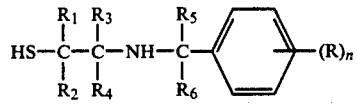

wherein R is $-COOR_7$, $-CONHR_7$, $-OH$, $-SO_3H$ or $-SO_3R_8$; $R_1$, $R_2$, $R_3$, $R_4$, $R_5$ and $R_6$ each independently is hydrogen or alkyl having from 1 to 6 carbon atoms; $R_7$ is hydrogen or alkyl having from 1 to 6 carbon atoms; $R_8$ is an alkali metal; and n is 2 or 3; and the salts thereof.

2. The compound as defined in claim 1 wherein R is $-COOR_7$, $R_3$ and $R_4$ are methyl and n is 2; and the salts thereof.

3. A compound represented by the formula

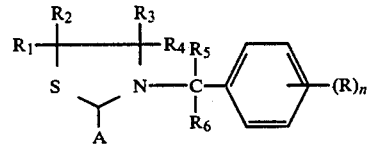

wherein A is hydrogen, alkyl having from 1 to 6 carbon atoms, phenyl, naphthyl, benzyl or phenethyl; R is $-COOR_7$, $-CONHR_7$, $-OH$, $-SO_3H$, or $-SO_3R_8$; $R_1$, $R_2$, $R_3$, $R_4$, $R_5$ and $R_6$ each independently is hydrogen or alkyl having from 1 to 6 carbon atoms; $R_7$ is hydrogen or alkyl having from 1 to 6 carbon atoms; $R_8$ is an alkali metal; and n is 2 or 3; and the salts thereof.

4. The compound as defined in claim 3 wherein $R_3$ and $R_4$ are methyl.